(12) United States Patent
Ahmad et al.

(10) Patent No.: US 11,433,016 B2
(45) Date of Patent: *Sep. 6, 2022

(54) COSMETIC COMPOSITIONS FOR SKIN

(71) Applicant: L'OREAL, Paris (FR)

(72) Inventors: Rabia Ahmad, Queens, NY (US);
Patricia Brieva, Manalapan, NJ (US);
Jaimie Mecca, Clifton, NJ (US);
Sabina Gosto, Piscataway, NJ (US)

(73) Assignee: L'OREAL, Paris (FR)

( * ) Notice: Subject to any disclaimer, the term of this patent is extended or adjusted under 35 U.S.C. 154(b) by 15 days.

This patent is subject to a terminal disclaimer.

(21) Appl. No.: 16/367,501

(22) Filed: Mar. 28, 2019

(65) Prior Publication Data
US 2020/0306167 A1 Oct. 1, 2020

(51) Int. Cl.
| A61K 8/894 | (2006.01) |
| A61K 8/25 | (2006.01) |
| A61K 8/49 | (2006.01) |
| A61K 8/893 | (2006.01) |
| A61K 8/92 | (2006.01) |
| A61Q 17/04 | (2006.01) |

(52) U.S. Cl.
CPC ............. *A61K 8/894* (2013.01); *A61K 8/25* (2013.01); *A61K 8/4946* (2013.01); *A61K 8/893* (2013.01); *A61K 8/922* (2013.01); *A61Q 17/04* (2013.01); *A61K 2800/31* (2013.01); *A61K 2800/612* (2013.01)

(58) Field of Classification Search
None
See application file for complete search history.

(56) References Cited

U.S. PATENT DOCUMENTS

| 5,741,509 | A | 4/1998 | Kushner |
| 6,503,944 | B1 * | 1/2003 | Chanchani ............... A61K 8/02 424/401 |
| 8,147,883 | B1 * | 4/2012 | Msika ..................... A61K 36/28 424/764 |
| 8,263,114 | B2 | 9/2012 | Berlat |

FOREIGN PATENT DOCUMENTS

| FR | 2992198 A1 * | 12/2013 | ............... A61Q 1/12 |
| WO | 0187232 A2 | 11/2001 | |

OTHER PUBLICATIONS

Machine translation, FR2992198 (Year: 2013).*

* cited by examiner

*Primary Examiner* — Bethany P Barham
*Assistant Examiner* — Barbara S Frazier
(74) *Attorney, Agent, or Firm* — Laetitia Leproust; Robert Klemz

(57) ABSTRACT

The present disclosure relates to anhydrous cosmetic compositions comprising: a) From about 0.1% to about 2% of one silica silylate; b) From about 0.1% to about 5% of allantoin; c) From about 0.1% to about 5% of at least one fatty substance; d) From about 2% to about 30% of at least one emulsifier; e) From about 20% to about 30% of at least a first silicone having a viscosity from about between 2 cst to about 70 cst; and f) From about 50% to about 95% of at least a second silicone; wherein all weight percentages are based on the total weight of the cosmetic composition.

21 Claims, 1 Drawing Sheet

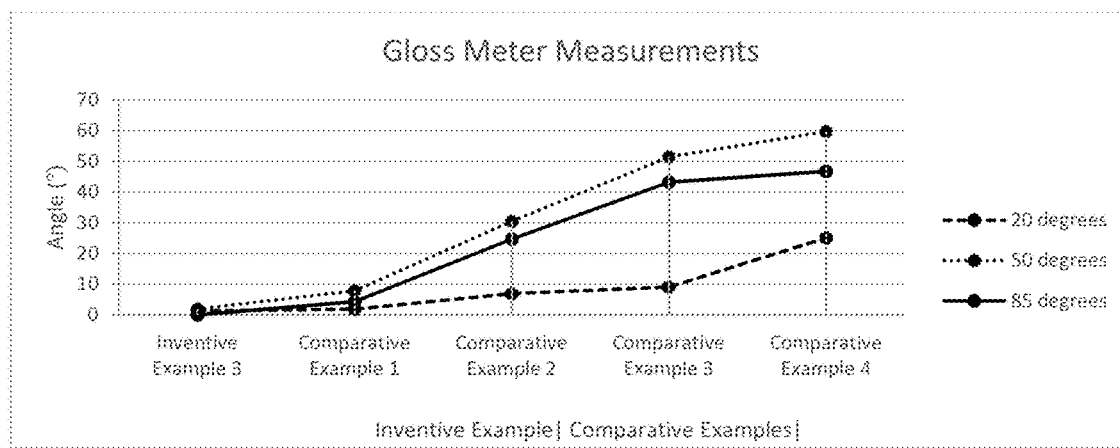

COSMETIC COMPOSITIONS FOR SKIN

FIELD OF THE DISCLOSURE

The present disclosure relates to a cosmetic composition. More specifically, the present disclosure is directed to an anhydrous composition containing allantoin and providing a barrier protection.

BACKGROUND

A variety of compositions, especially cosmetic compositions, have been developed to provide occlusive, transformative skin texture. Unfortunately, many of these compositions are in fact difficult to apply and do not possess a smooth feel upon application.

Although glycerin is a fairly low cost humectant or hydrating agent, problems arise when incorporating high levels of glycerin in cosmetic compositions. Incorporating high levels of glycerin, results in a cosmetic compositions having a tacky and sticky feel upon application to skin. The tacky or oily feel is undesirable to consumers. Several approaches, such as using light emollients, powders, or combinations thereof may reduce tackiness; however, the resulting cosmetic compositions may not provide sufficient consumer appeal and may still have residual tackiness that can be felt on the skin after application.

It is an object of the present disclosure to provide a cosmetic application that provides high glide and skin protection with an elegant feel. Yet another object of the present disclosure is to provide a favorable environment for skin healing/repair/skin protection.

SUMMARY OF THE DISCLOSURE

The instant disclosure relates to an anhydrous cosmetic composition the composition comprising:
 a) From about 0.1% to about 2% by weight of one silica silylate;
 b) From about 0.1% to about 5% by weight of allantoin;
 c) From about 0.1% to about 5% by weight of at least one fatty substance;
 d) From about 2% to about 30% by weight of at least one emulsifier;
 e) From about 20% to about 30% by weight of at least a first silicone having a viscosity from about between 2 cst to about 70 cst; and
 f) From about 50% to about 95% by weight of at least a second silicone;
  wherein all weight percentages are based on the total weight of the cosmetic composition.

In one or more embodiments, the silica silylate is silica silylate particles and especially aerogel particles of hydrophobic silica surface-modified with trimethylsilyl groups. In some embodiments, the silica silylate is present in an amount from about 0.5% to about 1.5% by weight based on the total weight of the composition.

In one or more embodiments, the allantoin is present in an amount from about 0.1% to about 5% by weight based on the total weight of the composition. In more embodiments, the allantoin is present in an amount from about 0.4% to about 3% by weight based on the total weight of the composition.

In some embodiments, the at least one fatty substance is selected from butters of plant origin, hydrogenated plant oils, and mixtures thereof. In one embodiment, the at least one fatty substance is selected from mango butter, cocoa butter; the mixture of mimosa, *Helianthus Annuus* (sunflower) Seed Oil Unsaponifiables; jojoba and sunflower plant waxes; hydrogenated jojoba oil, and mixtures thereof.

In some embodiments, the at least one emulsifier comprises an organosiloxane emulsifier. In one or more embodiments, the organosiloxane emulsifier is a crosslinked organosiloxane emulsifier selected from the group consisting of dimethicone crosspolymer, dimethicone/dimethicone crosspolymer, dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In one embodiment, the at least first silicone is having a viscosity from about between 4 cst to about 65 cst by weight based on the total weight of the composition.

In one or more embodiments, the at least second silicone is selected from the group consisting of dimethicone, cyclomethicone, polysilicone-11, phenyl trimethicone, trimethylsilylamodimethicone, and stearoxytrimethylsilane. In one or more embodiments, the at least second silicone has a viscosity of at least about 100 cSt. In more embodiments, the at least second silicone comprises dimethicone. In some embodiments, the at least second silicone is present from about 60% to about 90% of silicone by weight based on the total weight of the composition.

In one embodiment, the weight ratio of the emulsifier with the first silicone is about 0.4.

In one or more embodiments, the fatty substances are present in an amount from about 0.05% to about 5% by weight based on the total weight of the composition.

In some embodiments, the anhydrous cosmetic composition may further comprise one or more film formers. In one embodiment, one or more film formers are selected from the group consisted of acrylates/dimethicone crosspolymer, waxes and mixtures thereof.

In some embodiments, the anhydrous cosmetic composition may further comprise one or more active agents. In some embodiments, the one or more active agents are selected from the group consisting of adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme.

Another aspect of the instant disclosure can include an anhydrous cosmetic composition comprising:
 a) From about 0.1% to about 2% by weight of one silica silylate;
 b) From about 0.1% to about 5% by weight of allantoin;
 c) From about 0.1% to about 5% by weight of *Helianthus Annuus* (sunflower) Seed Oil Unsaponifiables;
 d) From about 2% to about 30% by weight of dimethicone crosspolymer
 e) From about 20% to about 30% by weight of a first silicone having a viscosity from about between 4 cst to about 65 cst by weight based on the total weight of the composition; and
 f) From about 60% to about 90% by weight of at least a second silicone selected from the group consisting of dimethicone, cyclomethicone, polysilicone-11, phenyl trimethicone, trimethylsilylamodimethicone, and stearoxytrimethylsilane;

wherein all weight percentages are based on the total weight of the cosmetic composition.

Another aspect of the present disclosure is a method for protecting skin comprising applying an effective amount of the sunscreen composition of the present disclosure to the skin.

The anhydrous cosmetic compositions of the instant disclosure provide an unexpected and unique texture that help to restore skin smoothness, reduce visual redness, improve skin tone evenness, flatten imperfections and improve skin firmness that can be spread on the skin very easily with a matte finish.

It is to be understood that both the foregoing general description and the following detailed description are exemplary and explanatory only, and are not restrictive of the invention.

BRIEF DESCRIPTION OF THE DRAWINGS

FIG. 1 is a graph showing Gloss Meter Measurements

It should be understood that the various aspects are not limited to the arrangements and instrumentality shown in the figures.

DETAILED DESCRIPTION OF THE DISCLOSURE

The instant disclosure relates to anhydrous cosmetic compositions.

The anhydrous cosmetic compositions of the instant disclosure, in their broadest sense, typically include the following:
a) From about 0.1% to about 2% by weight of one silica silylate;
b) From about 0.1% to about 5% by weight of allantoin;
c) From about 0.1% to about 5% by weight of at least one fatty substance;
d) From about 2% to about 30% by weight of at least one emulsifier;
e) From about 20% to about 30% by weight of at least a first silicone having a viscosity from about between 2 cst to about 70 cst; and
f) From about 50% to about 95% by weight of at least a second silicone;
wherein all weight percentages are based on the total weight of the cosmetic composition.

The anhydrous cosmetic compositions of the instant disclosure exhibit a surprisingly skin protection without feeling tacky or having a high shine. The compositions are particularly interesting in that they are helping to restore skin smoothness, reduce visual redness, improve skin tone evenness, flatten imperfections and improve skin firmness. Furthermore, the compositions spread easily, do not irritate skin through friction and do not feel tacky even though there is a high level of silicone.

As used herein, the term "anhydrous" means that no water is added to the composition and water is contained only in the form of the constitutional water which in some cases cannot be avoided and is brought in as part of the ingredients in very small amounts.

In some embodiments, the anhydrous cosmetic composition is essentially free of water. In one or more embodiments, the amount of water may be less than 0.5%. In some embodiments, the amount of water may be less than 0.1%. In one or more embodiments, the anhydrous cosmetic composition is free of water.

Silica Aerogel

According to the present disclosure, the anhydrous cosmetic composition may comprise at least one silica aerogel. Silica aerogels are porous materials obtained by replacing (by drying) the liquid component of a silica gel with air. They are generally synthesized via a sol-gel process in a liquid medium and then dried, usually by extraction with a supercritical fluid, the one most commonly used being supercritical $CO_2$. Drying of this type makes it possible to avoid contraction of the pores and of the material. The sol-gel process and the various drying operations are described in detail in Brinker C. J. and Scherer G. W., *Sol-Gel Science*, New York, Academic Press, 1990.

The hydrophobic silica aerogel particles used in the present invention have a specific surface area per unit of mass ($S_M$) ranging from 500 to 1500 $m^2/g$, preferably from 600 to 1200 $m^2/g$ and better still from 600 to 800 $m^2/g$, and a size expressed as the mean volume diameter (D[0.5]), ranging from 1 to 30 µm, preferably from 5 to 25 µm, better still from 5 to 20 µm and even better still from 5 to 15 µm.

The specific surface area per unit of mass may be determined via the BET (Brunauer-Emmett-Teller) nitrogen absorption method described in the *Journal of the American Chemical Society*, vol. 60, page 309, February 1938 and corresponding to the international standard ISO 5794/1 (appendix D). The BET specific surface area corresponds to the total specific surface area of the particles under consideration.

The size of the silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, N.Y., 1957.

The silica aerogel particles used in the present invention may advantageously have a tamped density r) ranging from 0.04 $g/cm^3$ to 0.10 $g/cm^3$ and preferably from 0.05 $g/cm^3$ to 0.08 $g/cm^3$.

In the context of the present disclosure, this density, known as the tamped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in $cm^3$ and m in g).

According to one embodiment, the hydrophobic silica aerogel particles used in the present disclosure have a specific surface area per unit of volume $S_V$ ranging from 5 to 60 $m^2/cm^3$, preferably from 10 to 50 $m^2/cm^3$ and better still from 15 to 40 $m^2/cm^3$.

The specific surface area per unit of volume is given by the relationship:

$S_V = S_M \cdot r$ where r is the tamped density expressed in g/cm$^3$ and $S_M$ is the specific surface area per unit of mass expressed in m$^2$/g, as defined above.

Preferably, the hydrophobic silica aerogel particles according to the disclosure have an oil-absorbing capacity, measured at the wet point, ranging from 5 to 18 mL/g, preferably from 6 to 15 mL/g and better still from 8 to 12 mL/g.

The oil-absorbing capacity measured at the wet point, noted Wp, corresponds to the amount of water that needs to be added to 100 g of particle in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in mL) of oil used is then noted. The oil uptake corresponds to the ratio Vs/m.

The aerogels used according to the present disclosure are aerogels of hydrophobic silica, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles surface-modified by silylation, reference may be made to U.S. Pat. No. 7,470,725.

Use will be made in particular of silylated silica aerogel particles and especially aerogel particles of hydrophobic silica surface-modified with trimethylsilyl groups (trimethylsiloxyl silica).

As hydrophobic silica aerogels that may be used in the disclosure, examples that may be mentioned include the aerogel sold under the name VM-2260 (INCI name: Silica silylate), by the company Dow Corning, the particles of which have an average size of about 1000 microns and a specific surface area per unit mass ranging from 600 to 800 m$^2$/g.

In other embodiments, the aerogels sold by the company Cabot under the names Aerogel TLD 201®, Aerogel OGD 201®, and Aerogel TLD 203®, CAB-O-SIL TS-530, CAB-O-SIL TS-610, CAB-O-SIL TS-720, Enova Aerogel MT 1100®, and Enova Aerogel MT 1200®, may be chosen.

Use will be made more particularly of the aerogel sold under the name VM-2270 (INCI name: Silica silylate) by the company Dow Corning, the particles of which have a mean size ranging from 5-15 microns and a specific surface area per unit mass ranging from 600 to 800 m$^2$/g. It has an oil absorption capability of 1090 mL/100 g based on isononyl isononanoate.

The silica silyliate may be present in an amount from about 0.1%, 0.2%, 0.3%, 0.4%, 0.5%, 0.6%, 0.7%, 0.8%, 0.9% to about 0.9%, 1%, 1.2%, 1.4%, 1.6%, 1.8%, or to 2% by weight based on the total weight of the composition.

Allantoin

Examples of suitable active ingredient in solid form which may be mentioned include, but are not limited to, vitamin C, alpha hydroxy acids, calamine, allantoin, refreshing active agents such as menthol, proteins and protein hydrolysates, sugar and derivatives thereof, glycyrrhetinic acid, and UV blockers. Preferred among the active ingredients in solid form is allantoin.

The active ingredient will typically be present in the composition in an amount from 0.01%, 0.02%, 0.03%, 0.04%, 0.05%, 0.1%, 0.15%, 0.2%, 0.25%, 0.3%, 0.35%, 0.4%, 0.5%, 0.6%, 0.7%, 0.8%, 0.9%, 1%, 1.5% to about 1.5%, 2%, 2.5%, 3%, 3.5%, 4%, 4.5%, or 5% by weight based on the total weight of the composition.

Fatty Substance

The at least one fatty substance is selected from butters of plant origin, hydrogenated plant oils, and mixtures thereof. Non-limiting samples of fatty substance can be selected from mango butter, cocoa butter; the mixture of mimosa, *Helianthus Annuus* (sunflower) Seed Oil Unsaponifiables; jojoba and sunflower plant waxes; hydrogenated jojoba oil; and mixtures thereof.

The anhydrous cosmetic compositions of the disclosure can include one fatty substance that are hydrocarbon-based, preferably selected from plant oils. In some embodiments, the fatty substance may be, for example, selected from the group consisting of olive oil, coconut oil (Cocos Nucifera Oil), avocado oil (Persea Gratissima oil), apricot oil, sweet almond oil, castor oil, coriander oil, grapeseed oil, rapeseed oil, hazelnut oil, shea butter, palm oil, apricot kernel oil, rice bran oil (Oryza Sativa (rice) Bran Oil), corn germ oil (Zea Mays Oil, wheatgerm oil, soybean oil, sunflower oil, evening primrose oil, safflower oil, sesame seed oil, passionflower oil, camellia oil, Vitis Vinifera (grape) Oil, and mixtures thereof.

While oils of plant origin are preferred, other hydrocarbon-based oils of mineral or synthetic origin are also useful. Such oils include, for example, volatile or non-volatile liquid paraffins and derivatives thereof, petroleum jelly, mineral oil, perhydrosqualene, polydecenes, isohexadecane, isododecane, and hydrogenated polyisobutene such as Paream™ oil (sold by NOF Corp.), and mixtures thereof.

Other non-silicone fats useful in the invention include, for example, esters and carbonates, as well as triglycerides. Examples of useful esters include C12-15 alkyl benzoate, cetearyl isononanoate, cetyl ethylhexanoate, coco-caprylate/caprate, decyl oleate, ethylhexyl stearate, hexyl laurate, isopropyl myristate, isopropyl palmitate, oleyl erucate, and mixtures thereof.

Examples of carbonates include dicaprylyl ether (available as Cetiol OE from Cognis) and dicaprylyl carbonate (Cetiol CC also from Cognis), Examples of tryglicerides include caprylic/capric triglyceride (sold by Cremer Oleo GmbH & Co. as MIGLYOL® 810 and 812) and caprylic/capric linoleic triglyceride (sold by Cremer Oleo GmbH & Co. as MIGLYOL® 818 and 829), and mixtures thereof.

In some embodiments, the fatty substance may be present in an amount from about 0.1%, 0.2%, 0.3%, 0.4%, 0.5%, 0.6%, 0.7%, 0.8%, 0.9%, 1%, 1.2%, 1.4%, 1.6%, 1.8%, 2%, 2.2%, 2.4% to about 2.4%, 2.6%, 2.8%, 2.9%, 3%, 3.2%, 3.4%, 3.6%, 3.8%, 4%, 4.2%, 4.5%, 4.8%, or 5% by weight based on the total weight of the composition.

*Helianthus Annuus* (sunflower) Seed Oil Unsaponifiables (=also known as Soline)

In some embodiments, the presence of *Helianthus Annuus* (sunflower) Seed Oil Unsaponifiables helps to reduce the redness and irritation of the skin.

In some embodiments, when the anhydrous cosmetic compositions further comprise one or more fatty substance, the fatty substance may be present in an amount from about 0.05%, 0.1%, 0.15%, 0.2%, 0.25%, 0.3%, 0.35%, 0.4%, 0.5%, 0.6%, 0.7%, 0.8%, 0.9%, 1%, 1.5% to about 1.5%, 1.8%, 2%, 2.2%, 2.4%, 2.6%, 2.8%, 3%, 3.4%, 3.8%, 4%, 4.4%, 4.6%, 4.8%, or 5% by weight based on the total weight of the composition.

Emulsifiers

Suitable examples of emulsifiers include polyether substituted linear or branched polysiloxane copolymers. For example, the emulsifier can be selected from dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone, dimethicone (and)dimethicone/PEG-10/15 crosspolymer PEG/PPG-18/18 dimethicone, dimethicone/dimethicone crosspolymer, dimethicone (and)dimethicone/polyglycerin-3 crosspolymer and combinations thereof. One preferred co-emulsifier is PEG-10 dimethicone available under the tradename of ES-5612 from Dow Corning Corporation (Midland, Mich.), or KF-6017 from Shin-Etsu (Akron, Ohio). One preferred emulsifier is polydimethyl siloxane available under the tradename of Dowsil EI-9241 DM Silicone Elastomer Blend; Dow Corning EI-9241 Dm Silicone Elastomer Blend from Dow Corning Corporation (Midland, Mich.). Another preferred emulsifier is dimethicone (and) PEG/PPG-18/18 dimethicone available under the tradename of ES-5226 DM from Dow Corning Corporation (Midland, Mich.). other suitable emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio).

The at least one emulsifier may be present in an amount from about 2%, 3%, 4%, 5%, 6%, 6.5%, 7%, 7.5%, 8%, 8.5%, 9%, 9.5%, 10%, 10.5%, 11%, 12% to about 13%, 14%, 15%, 16%, 17%, 18%, 19%, 20%, 22%, 24%, 25%, 28%, or 30% by weight based on the total weight of the composition.

Silicones

Useful silicones include, but are not limited to, polyorganosiloxanes, polyalkylsiloxanes, polyarylsiloxanes, polyalkarylsiloxanes, polyestersiloxanes, and a mixture thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a mixture thereof.

In some instances, the compositions include one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, and mixtures thereof.

First Silicone

Examples of silicones with a low viscosity and that may be mentioned include those with a viscosity from about 2 cst to about 70 cst. In some embodiments, the viscosity of the silicones might be from about 2 cst, 3 cst, 4 cst, 5 cst, 6 cst, 7 cst, 8 cst, 10 cst, 12 cst, 14 cst, 16 cst, 18 cst, 20 cst, 22, cst, 24 cst, 26 cst, 28 cst, 30 cst, 35 cst, 40 cst to about 40 cst, 42 cst, 44 cst, 46 cst, 48 cst, 50 cst, 52 cst, 54 cst, 56 cst, 58 cst, 60 cst, 62 cst, 64 cst, 66 cst, 68 cst, or 70 cst.

Non-limiting examples include Dow Corning® 200 Fluids, DC 200® fluid, DC 200 silicone, Dow Corning® Silicone, Dow Corning® Dimethicone, GE SF96 Silicone, SF96 Silicone, Wacker AK Fluids, Baysilone Dimethicones, Bayer-Baysilone Silicone, Shinetsu Silicone, Shinetzu Dimethicone, cosmetic grade silicone, personal care dimethicone The amount of the at least first silicone may be in an amount of about 20%, 21%, 22%, 23%, 24%, 25% to about 25%, 26%, 27%, 28%, 29%, or 30% by weight based on the total weight of the composition.

Second Silicone

Examples of silicones having a high viscosity that may be mentioned include those with a viscosity from at least about 100 cst or even more.

Non-limiting examples include dimethicone, cyclomethicone, polysilicone-11, phenyl trimethicone, trimethylsilylamodimethicone, and stearoxytrimethylsilane.

Other non-limiting examples of silicones having a high viscosity higher than that of the first silicone include those non-emusifying silicones that are available in combination with emulsifying silicones in the following combinations: Cyclopentasiloxane (and) PEG/PPG-19/19 Dimethicone, PEG/PPG-19/19 Dimethicone (and) C13-16 Isoparaffin (and) C10-13 Isoparaffin, Dimethicone (and) PEG/PPG-18 Dimethicone, Cyclopentasiloxane (and) and PEG/PPG-18/18 Dimethicone, Dimethicone (and) PEG/PPG-18/18 Dimethicone.

Non-limiting examples of silicones having a high viscosity higher than that of the first silicone are commercially available under the following tradenames: Dow Corning 200® Fluid, 100cs, Dow Corning 200®, 200cs, Dow Corning 200®350cs, Dow Corning 200®5000cs, Dow Corning 200®1000cs, GE SF96-100cs, GE SF96-200cs, GE SF 96-350, GE SF96-500, and GE SF96-1000.

In one embodiment, the second silicone is available as DOWSIL EL-9140 DM Silicone Elastomer Blend.

The amount of the at least second silicone may be in an amount of about 50%, 52%, 54%, 56%, 58%, 60%, 61%, 62%, 63%, 64%, 65%, 66%, 67%, 68%, 69%, 70%, 72%, 74% to about 74%, 76%, 78%, 80%, 82%, 84%, 86%, 88%, or 90% by weight based on the total weight of the composition Film Former The anhydrous cosmetic composition according to the disclosure, may further include a film former. In some embodiments, suitable example of film formers includes, but are not limited to, Trimethylsiloxysilicate (and) polypropylsilsesquioxane, Acrylates/Polytrimethylsiloxymethacrylate Copolymer, Dimethicone (and) Acrylates/dimethicone copolymer, Polypropylsilsesquioxane, Trimethylsiloxysilicate), Crotonic acid/vinyl C8-12, Isoalkyl Esters/Va/Bis-Vinyldimethicone Crosspolymer.

The film former may be present in an amount from about 0.01%, 0.02%, 0.05%, 0.08%, 0.1%, 0.2%, 0.25%, 0.3%, 0.35%, 0.4%, 0.5%, 0.6%, 0.7%, 0.8%, 0.9%, 1%, 1.5%, to about 1%, 1.5%, 2%, 2.5%, 3%, 3.5%, or 4% by weight based on the total weight of the composition.

Active Agents

The anhydrous cosmetic composition according to the disclosure, may further include one or more active ingredients. The cosmetic composition according to the disclosure includes an active ingredient from about 0.01% to about 5% by weight based on the total weight of the composition. In one embodiment, the active ingredient is capryloyl salicylic acid, adenosine, baicalin, resveratrol, other polyphenols, or combinations thereof. In another embodiment, the active ingredient is an organic or inorganic UV filter, or combination thereof. In some embodiments, the active ingredient is selected from humectant, antimicrobial, antioxidant, preservative, vitamin, vitamin derivative, UV filter, vegetable extract; and dye/pigment, filler, thickener, polymer, penetrant, fragrance, dispersant, film-forming agent; ceramide; opacifier and combinations thereof. In one embodiment, one or more actives can be selected from sodium hydroxide, disodium EDTA, sodium citrate, sodium hyaluronate, capryloyl salicylic acid, lactic acid, methyl dihydro jasmonate, acetyl trifluoromethyl phenyl valyglycine, pentaerythrityl tetra-di-t-butyl hydroxydrocinnamate, n-hydroxysuccinimide, palmitoyl oligopeptide, chrysin, palmitoyl tetrapeptide-7, yeast extract, citric acid and combinations thereof.

Fragrance

Fragrance including natural or synthetic odoriferous substances or mixtures thereof may be included in the cosmetic composition of the present disclosure. Use may be made of mixtures of different odoriferous substances which together generate an attractive scent. Natural odoriferous substances are extracts of flowers (lily, lavender, rose, jasmine, neroli or ylang-ylang), stems and leaves (geranium, patchouli, petitgrain), fruits (anis, coriander, caraway, juniper), fruit rinds (bergamot, lemon, orange), roots (mace, angelica, celery, cardamom, costus, iris, thyme), needles and twigs (spruce, fir, pine, mountain pine) and resins and balsams (galbanum, elemi, benzoin, myrrh, frankincense, opoponax). Typical synthetic perfume compounds are products of the esters, ethers, aldehydes, ketones, alcohols and hydrocarbon types. Essential oils of low volatility, which are generally used as flavoring components, are also suitable as fragrances, for example, but not limited to, sage oil, camomile oil, clove oil, balm oil, peppermint oil, cinnamon leaf oil, linden blossom oil, juniper berry oil, vetiver oil, frankincense oil, galbanum oil, labdanum oil and lavandin oil.

The composition of the present disclosure may also contain cosmetically acceptable additives or adjuvants as well as cosmetic or dermatologic active agents. Representative additives and adjuvants include, for example, water-soluble or water-miscible solvents or co-solvents, dispersion enhancing agents, moisturizers, colorants, fillers, antioxidants (e.g., EDTA, BHT, tocopherol), essential oils, fragrances, dyes, neutralizing or pH-adjusting agents (e.g., citric acid, triethylamine (TEA) and sodium hydroxide), conditioning or softening agents (e.g., panthenol and allantoinin) and extracts such as botanical extracts. Additives and adjuvants may be present in the compositions in amounts generally ranging from about 0.01% to about 10% by weight. Examples of cosmetic active agents or dermatological active agents include sunscreen agents (e.g., inorganic sunscreen agent, such as titanium dioxide and zinc oxide and organic sunscreen agents, such as octocrylene, ethylhexyl methoxycinnamate, and avobenzone), free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase).

More exhaustive but non-limiting lists of components useful in the hair care compositions disclosed herein are presented below.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

EXAMPLES

The following Examples are provided for illustrative purposes only, and are not intended to be limiting.

Example 1: Inventive Examples

Inventive Compositions were prepared and are presented in Table 1, below.

TABLE 1

| INCI US Name | Inventive Example 1 | Inventive Example 2 | Inventive Example 3 |
|---|---|---|---|
| Silica Silylate | 1 | 1 | 1 |
| Allantoin | 0.5 | 0.5 | 0.5 |
| Fatty substance | 2 | 2 | 2 |
| Helianthus Annuus (Sunflower) Seed Oil Unsaponifiables | | | |
| Helianthus Annuus Seed Oil Unsaponifiables (SOLINE) | | | |

TABLE 1-continued

| INCI US Name | Inventive Example 1 | Inventive Example 2 | Inventive Example 3 |
|---|---|---|---|
| Emulsifier Dimethicone Crosspolymer | 10.8 | 10.8 | 10.8 |
| First silicone 5 cst dimethicone | 24.5 | 24.5 | 21.5 |
| Second silicone Dimethicone | 61.2 | 61.2 | 62.4 |
| Film former (optional) | 0 | 0 | 0.8 |
| Additional Fatty substances (optional) | 0 | 1 | 1 |

In making the formulations in the above tables, the following procedure was used.

1. First Silicone and allantoin were added to steel beaker. Then, ran under Silverson at 5000 RPM for 15-minutes or until fully dispersed (no large particles). In between mixing, the sides of beaker were wiped by using a spatula.
2. The above phase was transferred into main kettle (ESCO), if present in composition, a fatty substance was added, and the phase was then heated to 75 C. The phase was mixed using scraper at 30% and homogenizer at low 10% (without splashing).
3. The phase was mixed until the fatty substance was melted.
4. The dimethicone crosspolymer and second silicone??? were added and removed from the heating jacket. The mixing was continued (50% scraper and homogenizer at 20%).
5. Once homogeneous, the *Helianthus Annuus* (Sunflower) Seed Oil Unsaponifiables *Helianthus Annuus* Seed Oil Unsaponifiables was added and mixing was continued (50% scraper and homogenizer at 20%).
6. Once homogeneous and if desired, a film former was added and mixing was continued (50% scraper and homogenizer at 20%).
7. Once homogeneous the silica silylate was added using a funnel (cover with plastic wrap to avoid particles released into air) while continuing to mix.
8. To ensure all silica silylate was mixed, spatula was used to wipe kettle and scraper.

The three examples above were considered Inventive Examples. The addition of a film former and/or other fatty substances was considered optional. The addition of the film former added a slight boost in sensorial experience. The addition of other fatty substances helped in the overall sensorial feeling of the compositions as well.

Example 2: Comparative Examples

TABLE 2

| INCI US Name | | Inventive Example 1 | Comparative Example 1 |
|---|---|---|---|
| Silica Silylate | Silica aerogel | 1 | 1 |
| Allantoin | Skin Protectant | 0.5 | 0.5 |
| *Helianthus Annuus* (Sunflower) Seed Oil Unsaponifiables *Helianthus Annuus* Seed Oil Unsaponifiables (SOLINE) | Solid fatty substance | 2 | 2 |
| Dimethicone Crosspolymer | Blurring effect associate with silica aerogel | 10.8 | 10.8 |
| 5 cst dimethicone | Silicone Oil | 24.5 | 0 |
| Dimethicone | Silicone oil | 61.2 | 86.2 |

The Inventive Example 1 and Comparative Example 1 were prepared following the procedure described above. The Inventive Example 1 was a blend of high concentration of silicones with dimethicone crosspolymer that created a barrier in the skin and results in a blur finish. In the Inventive Example 1, a low viscosity dimethicone (5 cSt) was used. After the application of the Inventive Example 1 on the skin, it was observed that the skin was smoother and well moisturized. It was also observed that this application reduced the irritation of the skin and reduce the redness due to irritation. A significant blurring effect was also observed.

In the case of Comparative Example 1, there was no low viscous dimethicone 5 cSt, but it was compensated by a higher concentration of silicone. It was observed that the Comparative Example 1 was not stable. Indeed, two separate layers were formed: the bottom layer formed a foggy layer and the top layer formed a clear layer. In addition, it did not exhibit the qualities observed for Inventive Example 1 and recited above, such as a skin protectant and a blur finish.

In conclusion, the presence of a low viscosity dimethicone (5 cst) blend in a certain ratio with a dimethicone crosspolymer showed that the combination of both was important and necessary to obtain a composition that stable and reduces visual redness and improves skin smoothness (visual and tactile), skin tone evenness, skin firmness, and flattens imperfections.

Example 3: Commercial Products

The present disclosure was compared to several commercially available products presented in Table 3, below.

TABLE 3

| Inventive and Comparative Examples | | | | |
|---|---|---|---|---|
| Product # | Technology | Actives | Stability | Differences |
| Comparative Ex. 3 | Anhydrous Silicone: polysiloxanes, silicon dioxide. | No Active | 8 Week Stability - Unstable | Although an anhydrous system, product does not contain actives and is unstable (on application and observed on microscope). Application is also heavy and shiny. |
| Comparative Ex. 4 | O/W Emulsion - Proloxamer 407, Xanthan Gum | Centelline ™ | 8 Week Stability - Stable | System contains water. Formula is sticky and has drag on application. |

TABLE 3-continued

Inventive and Comparative Examples

| Product # | Technology | Actives | Stability | Differences |
|---|---|---|---|---|
| Inventive Ex. 3 | Anhydrous silicone | Allantoin - 0.5% Sunflower Oil - 2% | 12 week stability - Stable | Anhydrous system Contains two actives Has passing 12-week stability Smooth and matte-finish application |

The Comparative Examples were sold as skin protective compositions offering a gentle/smooth application and a matte barrier. Nonetheless, they also presented negative characteristics such as instability after 8 weeks and/or imparting high shine to skin.

For example, Comparative Ex. 3 was anhydrous and the formula architecture was based on polysiloxanes siliconesa and did not contain allantoin or silica silylate. It was observed that even though it was anhydrous, the product was unstable after 8-weeks study. Plus, it was heavy and shiny on skin upon application. The Comparative Ex. 3 differed from the Inventive Ex. 3 mainly by the absence of a blend of a low viscosity dimethicone (5 cst) and a dimethicone crosspolymer which are believed to contribute to the stability of the inventive examples. It also differed by the absence of silica silylate contributes to a matte-finish and ease/smooth application, both properties not observed in comparative Ex. 3.

In the case of Comparative Ex. 4, the system contained an active called Centelline that helps with redness. It also presented a good stability, but the architecture formula was a O/W emulsion. Furthermore, the formula was sticky and was dragging upon application. So even though the stability was good, the properties exhibited by the inventive formula were better.

The Inventive Ex. 3 was put on stability at 4 C, 25 C, 37 C and 45 C with no stability issues after 12-weeks. Formula specifications including viscosity and aspect (appearance, odor and color) were not compromised with extreme temperatures over 12-weeks testing period. Certain comparative products separated at 25 C within 8-weeks (i.e. Comparative Ex. 3).

Example 4: Measurement of the Matte Finish Using a Gloss Meter

The matte finish of the inventive formulas and the commercially available products were measured using a Gloss Meter. The results are represented in the Table below and graphically shown in FIG. 1.

TABLE 5

Measurement of the gloss of different formulas (Mean Values)

| Examples | 20° (G.U.)* | 60° (G.U.)* | 85° (G.U.)* |
|---|---|---|---|
| Inventive Example 3 | 1.3 | 1.9 | 0 |
| Comparative Example 1 | 1.9 | 7.9 | 4.3 |
| Comparative Example 2 | 6.9 | 30.5 | 24.7 |
| Comparative Example 3 | 9.1 | 51.5 | 43.2 |
| Comparative Example 4 | 25.1 | 59.8 | 46.8 |

*G.U. = Gloss Unit

The following procedure was used to measure the gloss and determine the matte finish of the formula. Gloss is measured by shining a known amount of light at a surface and quantifying the reflectance. The angle of the light and the method by which the reflectance is measured are determined by the surface.

Gloss is measured using a Gloss Meter also known as a Glossmeter which directs a light at a specific angle to the test surface and simultaneously measures the amount of reflection. The type of surface to be measured determines the gloss meter angle to be used and thus the gloss meter model.

20°=high gloss coatings, plastics, brightened metal and similar materials
60°=medium (semi) gloss coatings, plastics, brightened metal and similar materials
85°=low gloss coatings, plastics, brightened metal and similar materials The intensity is dependent on the material and the angle of illumination. In case of nonmetals (coatings, plastics) the amount of reflected light increases with the increase of the illumination angle. The remaining illuminated light penetrates the material and is absorbed or diffusely scattered dependent on the color.

In the present disclosure, three measurements were taken along the film (manually moved by user) and each angle were measured at the same point. The average was automatically taken of the three values. A mean value and standard deviation value were provided for each angle. All measurements were taken upon initial film casting (0-1 minute).

In the instant disclosure, Inventive Example 3 show little to no shine by exhibiting the lowest number at the three different angles measurement. The numbers went from 1.3, 1.9 to 0. These means values demonstrated that the Inventive Example 3 had a matte finish compare to the other Comparative Examples; r.g., for Comparative Examples 3 and 4, the mean values were higher numbers, and consequently were shinier that the inventive examples. These results are also shown in FIG. 1 at different degree angles.

What is claimed:
1. An anhydrous cosmetic composition comprising:
a) From about 0.1% to about 2% by weight of one silica silylate;
b) From about 0.1% to about 5% by weight of allantoin;
c) From about 0.1% to about 5% by weight of at least one fatty substance;
d) From about 2% to about 20% by weight of at least one emulsifier;
e) From about 20% to about 30% by weight of at least one first silicone is a dimethicone having a viscosity from about between 2 cst to about 70 cst; and
f) From about 50% to about 70% by weight of at least one second silicone;
wherein all weight percentages are based on the total weight of the cosmetic composition, and
wherein the anhydrous cosmetic composition is free of dyes, pigments, and colorants.

2. The anhydrous cosmetic composition of claim 1, wherein the silica silylate is hydrophobic silica surface-modified with trimethylsilyl groups.

3. The anhydrous cosmetic composition of claim 2, wherein the silica silylate is present in an amount from about 0.5% to about 1.5% by weight based on the total weight of the composition.

4. The anhydrous cosmetic composition of claim 1, wherein the allantoin is present in an amount from about 0.1% to about 4% by weight based on the total weight of the composition.

5. The anhydrous cosmetic composition of claim 4, wherein the allantoin is present in an amount from about 0.4% to about 3% by weight based on the total weight of the composition.

6. The anhydrous cosmetic composition of claim 1, wherein the at least one fatty substance is selected from butters of plant origin, hydrogenated plant oils, and mixtures thereof.

7. The anhydrous cosmetic composition of claim 6, wherein the at least one fatty substance is selected from mango butter, cocoa butter, a mixture of *mimosa, Helianthus Annuus* (sunflower) Seed Oil Unsaponifiables, jojoba plant wax, sunflower plant waxes, hydrogenated jojoba oil, and mixtures thereof.

8. The anhydrous cosmetic composition of claim 1, wherein the at least one emulsifier comprises an organosiloxane emulsifier.

9. The anhydrous cosmetic composition of claim 8, wherein the organosiloxane emulsifier is a crosslinked organosiloxane emulsifier selected from the group consisting of dimethicone crosspolymer, dimethicone/dimethicone crosspolymer, dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer;

dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

10. The anhydrous cosmetic composition of claim 1, wherein the at least one first silicone has a viscosity from between about 4 cst to about 65 cst by weight based on the total weight of the composition.

11. The anhydrous cosmetic composition of claim 1, wherein the at least one second silicone has a viscosity of at least about 100 cSt.

12. The anhydrous cosmetic composition of claim 11, wherein the at least one second silicone comprises dimethicone.

13. The anhydrous cosmetic composition of claim 1, wherein the at least one second silicone is present from about 60% to about 70% by weight based on the total weight of the composition.

14. The anhydrous cosmetic composition of claim 1, wherein the at least one fatty substance is present in an amount from about 0.5% to about 5% by weight based on the total weight of the composition.

15. The anhydrous cosmetic composition of claim 1, further comprising one or more film formers.

16. The anhydrous cosmetic composition of claim 15, wherein one or more film formers are selected from the group consisting of acrylates/dimethicone crosspolymer, waxes and mixtures thereof.

17. The anhydrous cosmetic composition of claim 1, further comprising:
 g) One or more active agents.

18. The cosmetic composition of claim 17, wherein the one or more active agents are selected from the group consisting of adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, a coenzyme, and mixtures thereof.

19. An anhydrous cosmetic composition comprising:
 a) From about 0.1% to about 2% by weight of one silica silylate;
 b) From about 0.1% to about 5% by weight of allantoin;
 c) From about 0.1% to about 5% by weight of *Helianthus Annuus* (sunflower) Seed Oil Unsaponifiables;
 d) From about 2% to about 20% by weight of dimethicone crosspolymer,
 e) From about 20% to about 30% of at least one first silicone is a dimethicone having a viscosity from about between 4 cst to about 65 cst by weight; and
 f) From about 60% to about 70% by weight of at least one second silicone selected from the group consisting of dimethicone, cyclomethicone, polysilicone-11, phenyl trimethicone, trimethylsilylamodimethicone, and stearoxytrimethylsilane;
 g) Optionally from about 0.01 to about 5% of one or more active ingredients; and
 wherein all weight percentages are based on the total weight of the cosmetic composition, and
 wherein the anhydrous cosmetic composition is free of dyes, pigments, and colorants.

20. An anhydrous cosmetic composition comprising:
 a) From about 0.1% to about 2% by weight of one silica silylate;
 b) From about 0.1% to about 5% by weight of allantoin;
 c) From about 0.1% to about 5% by weight of at least one fatty substance;
 d) From about 2% to about 20% by weight of at least one emulsifier;
 e) From about 20% to about 30% by weight of at least one first dimethicone having a viscosity from about between 2 cst to about 70 cst; and
 f) From about 50% to about 70% by weight of at least one second dimethicone having a viscosity of at least about 100 cSt;
 wherein all weight percentages are based on the total weight of the cosmetic composition.

21. A method for protecting skin comprising applying an effective amount of the sunscreen composition of claim 1 to the skin.

* * * * *